United States Patent [19]

McGuire et al.

[11] Patent Number: 5,188,587
[45] Date of Patent: Feb. 23, 1993

[54] ACTIVE SHOULDER BRACE

[76] Inventors: Robert R. McGuire, 42192 Stonewood Rd., Apt. 12D, Temecula, Calif. 92390; James Weber, 26078 Charing Cross Rd., Valencia, Calif. 91355

[21] Appl. No.: 713,236

[22] Filed: Jun. 7, 1991

[51] Int. Cl.[5] .................................. A61F 5/00
[52] U.S. Cl. ........................... 602/20; 602/4; 602/62; 128/874; 2/45
[58] Field of Search ............... 602/4, 5, 12, 19, 20, 602/62, 63; 128/869, 874, 875, 876, 878; 2/16, 44, 45

[56] References Cited

U.S. PATENT DOCUMENTS

| | | | |
|---|---|---|---|
| 1,596,297 | 8/1926 | Oelgoetz | 602/19 |
| 3,906,944 | 9/1975 | Christen | 2/45 X |
| 4,188,944 | 2/1980 | Augustyniak | 602/20 |
| 4,446,858 | 5/1984 | Verter | 602/4 |
| 4,559,932 | 12/1985 | Salort | 602/20 |
| 4,598,703 | 7/1986 | Lindemann | 602/20 X |
| 4,644,939 | 2/1987 | Coleman | 602/19 |
| 4,735,198 | 4/1988 | Sawa . | |
| 4,784,128 | 11/1988 | Scheuermann | 602/63 X |
| 4,832,010 | 5/1989 | Lerman | 602/63 |
| 4,862,878 | 9/1989 | Davison et al. | 602/20 |
| 4,896,660 | 1/1990 | Scott | 602/20 |
| 4,947,870 | 8/1990 | Larcher | 602/19 X |

Primary Examiner—Richard J. Apley
Assistant Examiner—Linda C. M. Dvorak
Attorney, Agent, or Firm—Graham & James

[57] ABSTRACT

A shoulder brace comprising a resilient shoulder means conformable to the shoulder and upper arm of the wearer. The shoulder brace also includes a plurality of resilient torso straps each having a shoulder end which is attached to the shoulder means and an anchor end, and a plurality of resilient side straps each having a sleeve end which is attached to the shoulder means and a waist end. A waist belt is also provided which includes an overlap means for releasably affixing the waist belt about the waist of the user and a plurality of loop means in spatial relationship about the waist belt for removably securing each of the anchor ends and waist ends to the waist belt.

17 Claims, 5 Drawing Sheets

ACTIVE SHOULDER BRACE

FIELD OF THE INVENTION

This invention relates generally to orthopedic braces, and more particularly to an active shoulder brace for providing support to the shoulder area.

BACKGROUND OF THE INVENTION

The ball and socket joint of the human shoulder provides for free movement of the arm. The area of contact between the various bones in the shoulder is minimal and the shoulder joint is dependent upon the surrounding muscles, and to a lesser extent ligaments, tendons and fibrocartilage, for its integrity and functionality. The muscular and bone composition of the shoulder is the subject of extensive medical study and while a more detailed discussion of the anatomy of the shoulder is not necessary for the purposes here, such a discussion can be found in most basic human anatomy books. Because of its construction, the shoulder joint is capable of flexion, extension, abduction, adduction, rotation and circumduction movement. Also because of its construction, the shoulder joint is susceptible to a great number of injuries.

Injuries are commonplace in various activities that require constant motion of the shoulder joint or subject the shoulder to stress. For example, the overhand throwing motion used in baseball is an unnatural motion that can cause shoulder muscle strains or tears, including injury to the deep rotator muscles or "rotator cuff" of the shoulder and arm. Participants in contact sports such as rugby and football often suffer shoulder injuries, e.g., dislocation of the ball and socket joint, as well. Once an injury to the shoulder area has occurred, it is frequently necessary to support the joint area to both facilitate the convalescing process in certain situations, and minimize discomfort due to the injury. Additionally, it is advantageous to provide support to the shoulder area to help prevent shoulder injuries to individuals who are particularly susceptible to such injuries.

There are a number of braces and harnesses known in the art that alleviate pressure on various points of the shoulder joint. For example, U.S. Pat. No. 3,906,944 issued to Christen discloses a shoulder harness that prevents damage to the muscles, tendons and ligaments in the shoulder area and also provides support to prevent dislocation of the shoulder. The shoulder harness disclosed in the Christen Patent, however, severely restricts the movement of the upper arm with respect to the shoulder, thereby restricting the movement of the ball and socket joint. Most existing braces are cumbersome and difficult for a wearer to put on, particularly because of the shoulder injury. Most known braces and harnesses also neither allow the wearer to increase or decrease the amount of support around the area of the shoulder, nor are capable of being adjusted to conform to the particular body size of the wearer.

Additionally, because of the minimal impact and natural resistance that an aqueous environment provides, it is often preferable to undertake certain conditioning and rehabilitative exercise and training in water, e.g., swimming pool. Most existing shoulder braces, however, cannot be worn in the water because they include metal straps or buckles and cloth or leather materials that are subject to deterioration.

It should thus be apparent that existing shoulder braces and harnesses have inherent disadvantages that necessarily limit their use and functionality.

It is therefore desirable and an object of the present invention to provide a shoulder brace that serves both rehabilitative and preventive functions and provides support for the muscles, tendons and ligaments in the shoulder area without restricting the free movement of the arm. It is another object of the present invention to provide a shoulder brace that lessens the possibility of straining, overstretching or tearing the muscles, tendons and ligaments in the shoulder and upper arm area.

It is a further object of the present invention to provide a shoulder brace that lessens the possibility of dislocation of the shoulder ball and socket joint while permitting a full range of movement. It is a still further object of the present invention to provide a shoulder brace which can not only be adjusted to the physique of the individual wearer, but also can be adjusted so as to increase or decrease the amount of support around the shoulder area.

It is yet another object of the present invention to provide a shoulder harness which can be worn underneath clothing or athletic equipment, e.g., football or hockey shoulder pads, without interference or discomfort. And it is still another object of the present invention to provide a shoulder brace that can be worn in the water without absorbing the water into the brace material thereby avoiding any increase in the weight of the brace and without modifying its therapeutic, rehabilitative or support function and further without causing damage or deterioration to the brace.

SUMMARY OF THE INVENTION

The shoulder brace of the present invention meets the functional requirements discussed above in the Background of The Invention. Generally stated, the shoulder brace of the present invention includes a resilient shoulder means conformable to the shoulder and upper arm of a wearer. The shoulder means has a sleeve portion encasing the upper arm and a C-shaped shoulder member attached to the sleeve portion at the shoulder and extending downward therefrom. The shoulder brace also includes a plurality of resilient torso straps each having a shoulder end attached to the shoulder means and an anchor end, and a plurality of resilient side straps each having a sleeve end attached to the shoulder means and a waist end. A belt means for securing the shoulder brace about the waist is provided and includes a waist belt, an overlap means for releasably securing the waist belt in tension about the waist, and a plurality of loop means. The plurality of loop means are in spatial relationship about the waist belt and releasably secure each of the respective anchor ends and waist ends to the waist belt. Additionally, the anchor means and coupling means are of the hook-and-loop type fastening means.

In accordance with the preferred embodiment of the present invention, when the shoulder brace is worn, the plurality of resilient torso straps include a front torso strap and a back torso strap. The front torso strap extends from the shoulder down and across the front torso of the user and the anchor end attaches with the waist belt at a point in a spatial position below the back of the opposite shoulder. The back torso strap crosses from the back of the shoulder over and down the back torso of the user. The anchor end of the back torso strap attaching with the waist belt at a point in a spatial position below the front of the opposite shoulder. The front and back torso straps cross at a point below the shoulder area of the shoulder opposite the shoulder upon which the shoulder brace is being worn. Thus, the back torso strap is releasably attached to the waist belt at a point more forward on the body than the point where the front torso strap is releasably attached to the waist belt.

Similarly, the plurality of resilient side straps includes a front side strap and a back side strap. The front side strap crosses downward under the upper arm to the back torso of the wearer and the waist end of the front side strap is attached to the waist belt below the back of the shoulder. The back side strap crosses from the back of the shoulder under the upper arm to the front torso and is attached to the waist belt in a spatial position below the front of the shoulder. Similar to the situation in connection with the plurality of torso straps, the front and back side straps cross over at a point below the shoulder area of the shoulder upon which the shoulder brace is worn. The waist end of the front side strap is releasably attached to the waist belt at a point posterior to the point where the waist end of the back side strap releasably attaches to the waist belt. The attaching of the respective anchor ends and waist ends to the waist belt is achieved by a hook-and-loop type fastening means, and by the plurality of loop means.

It is believed that a better understanding of the present invention, as well as a recognition of how the present invention achieves the foregoing objects and attains various additional advantages, will become apparent to those sufficiently skilled in the art from a consideration of the following detailed description of the present invention and each of the alternative exemplary embodiments. During the detailed description, reference will be made to the appended sheets of drawings that are described briefly immediately below.

DETAILED DESCRIPTION OF THE DRAWINGS

Figure 1:
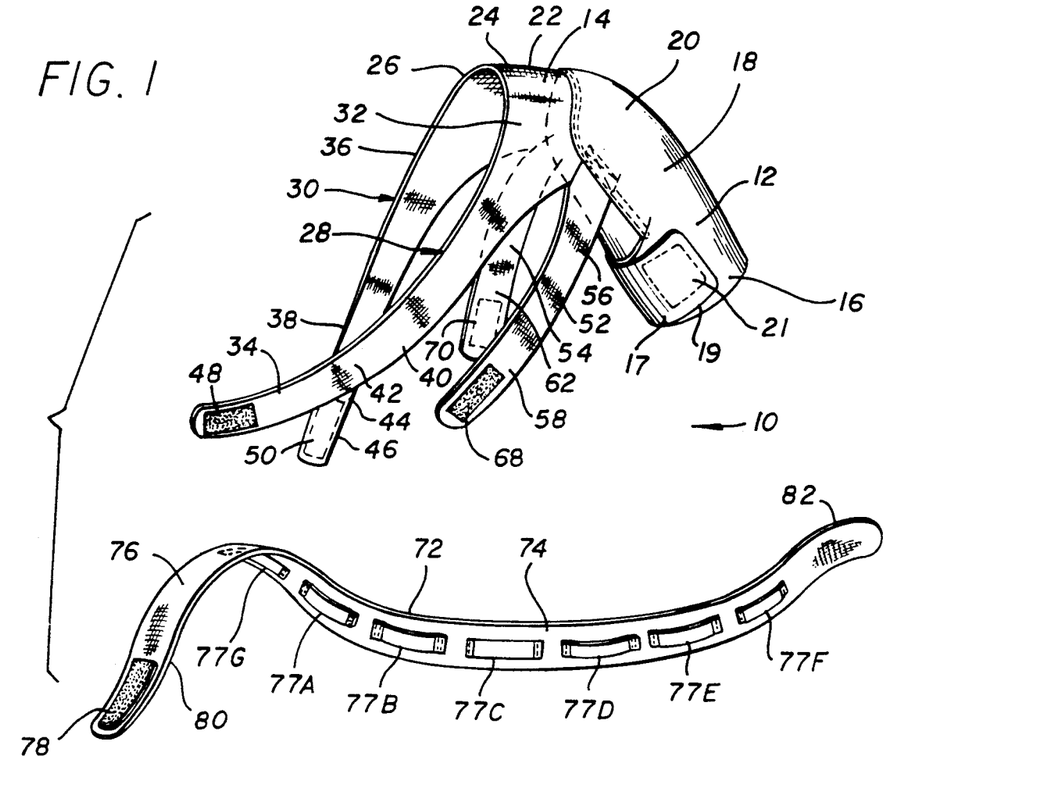
FIG. 1 is a front perspective view of a shoulder brace in accordance with the present invention.
Figure 2:
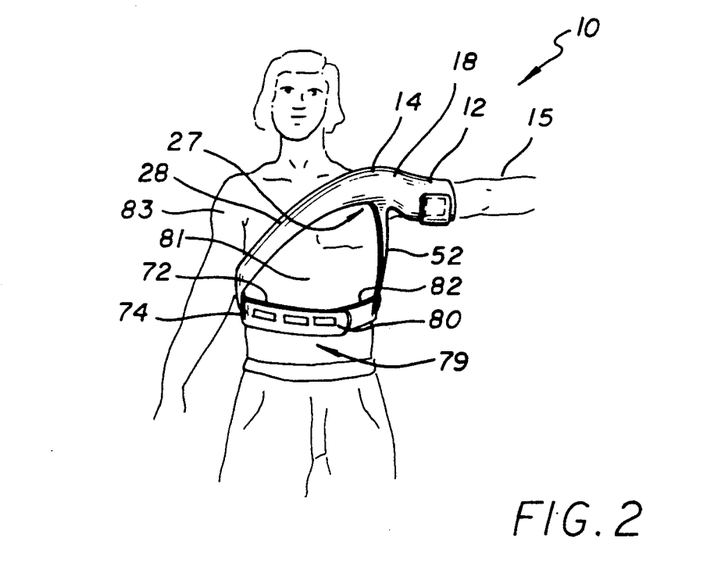
FIG. 2 is a front view of a shoulder brace in accordance with the present invention and being worn by a user.
Figure 3:
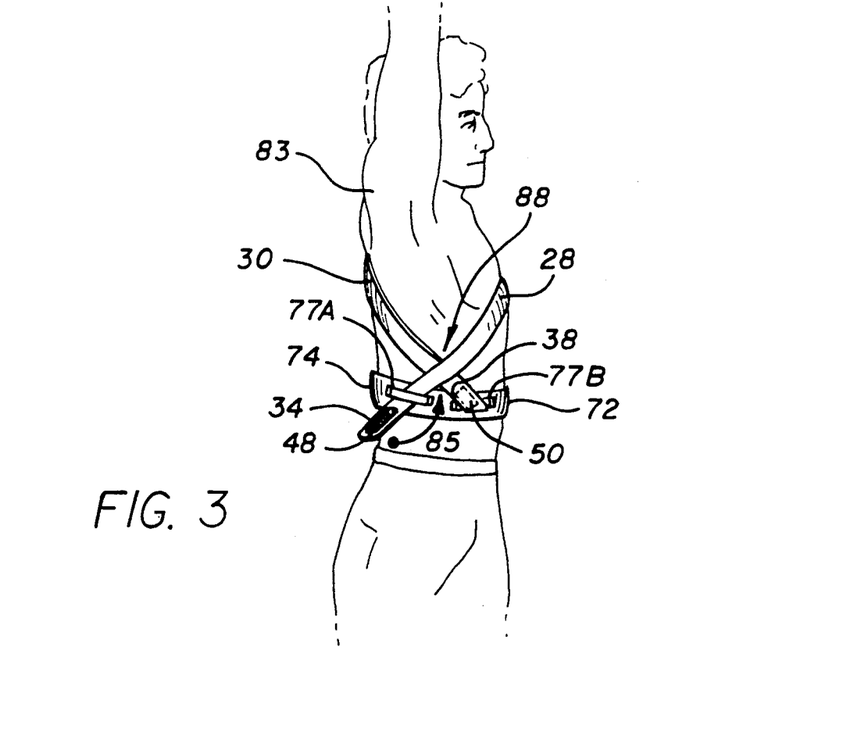
FIG. 3 is a first side view of a shoulder brace in accordance with the present invention and being worn by a user.
Figure 4:
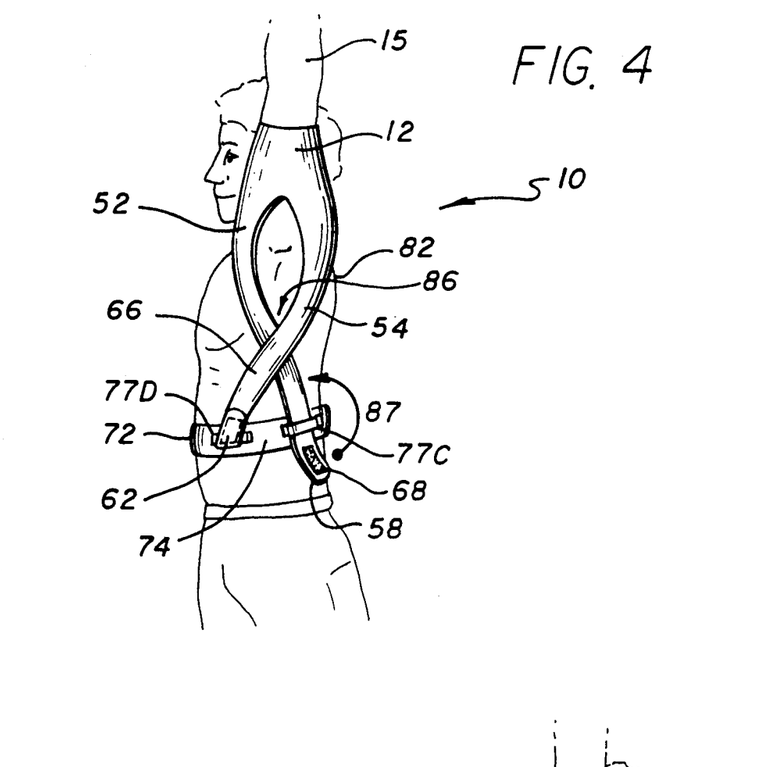
FIG. 4 is a second and opposite of FIG. 3 side view of a shoulder brace in accordance with the present invention and being worn by a user.

Referring now in detail to the drawings, FIG. 1 shows a front-perspective view of a shoulder brace in accordance with the present invention, and indicated generally at 10. Shoulder brace 10 has a sleeve portion 12 and a C-shaped shoulder member 14. Sleeve portion 12 has a lower sleeve area 16 and an upper sleeve area 18. Lower sleeve area 16 includes a sleeve tab 17 having an attachment end 19. Attachment end 19 adjustably encircles the arm 15 of the wearer and releasably engages with lower sleeve area 16 by use of a sleeve securing tab 21. As shown in the preferred embodiment, sleeve securing tab 21 comprises a releasable hook-and-loop type fastening means, i.e., synthetic materials that releasably adhere when pressed together. A variety of the hook-and-loop type securing means is sold under the trademark "VELCRO." It is, of course, contemplated that suitable fastening means other than the hook-and-loop type may be used. Further, it is within the scope of this invention that lower sleeve area 16 may be a one-piece, tubular shape and completely encircle the arm 15 of the wearer (as shown in FIG. 4). Upper sleeve area 18 is shown in the preferred embodiment to be a substantially C-shaped member with the open ended area on the under arm portion and terminating at upper sleeve end 20. Upper sleeve end 20 abuts shoulder member 14 of the shoulder brace 10. Shoulder brace 10 has top portion 22 and front and rear side portions 24 and 26, respectively. Shoulder member 14 is a generally flat member that is formable to the shape of a shoulder 27 of the user (as best shown in FIGS. 2 through 4).

Also shown in FIG. 1 are a plurality of resilient torso straps 28 and 30. Front torso strap 28 has a front shoulder end 32 and a front anchor end 34. Similarly, back torso strap 30 also has a back shoulder end 36 and a back anchor end 38. It should be clear that front torso strap 28 has an inner surface 40 and outer surface 42; and similarly, rear torso strap 30 also has an inner surface 44 and outer surface 46. The outer surface 42 of front anchor end 34 includes a first fastening strip 48 (shown in shadow lines on FIG. 1) attached to the anchor end 34 by a suitable means, e.g., adhesives or sewing. A second fastening strip 50 is similarly attached to the back anchor end 38 on the outer surface 46. The first and second fastening strips 48 and 50 are shown in the preferred embodiment to comprise a releasable hook-and-loop type fastening means.

A plurality of resilient side straps 52 and 54 are also shown in FIG. 1, the plurality of resilient side straps 52 and 54 comprises a front resilient side strap 52 and a back resilient side strap 54. Front resilient side strap 52 has a sleeve end 56 and waist end 58; and sleeve end 56 is connected to the upper sleeve area 18 of sleeve portion 12. Back resilient side strap 54 has a back sleeve end 60 and a back waist end 62. The back sleeve end 60 is affixed to the upper sleeve area 18 of sleeve portion 12.

Side straps 52 and 54 also include first and second coupling strips 68 and 70 affixed to the outer surfaces 64 and 66 of the respective waist ends 58 and 62. As shown in the preferred embodiment, coupling strips 68 and 70 and may be attached to waist ends 58 and 62 in the same method as was described previously with respect to first and second fastening strips 48 and 50.

With continuing reference to FIG. 1, a waist belt 72 is shown having a loop surface 74 and a body surface 76. Loop surface 74 includes a plurality of loop means in spatial relationship along loop surface 74. As shown in the preferred embodiment loop means are shown to be several tags or loops 77A, 77B, 77C, 77D, 77E, 77F and 77G. The number of loops may, of course, be varied. Loops 77A-G are capable of engaging with and spatially positioning anchor ends 34 and 38 and waist ends 58 and 62 as is discussed in detail below in connection with FIGS. 2 through 4.

Body surface 76 of waist belt 72 also includes a means for fastening the waist belt 72 about the waist region 79 of the user. A belt overlap strip 78 is located on the body surface 76 of waist belt 72 near belt end 80. The overlap strip 78 on waist belt 72 is shown as a releasable hook-and-loop type fastening means. The application and use of shoulder brace 10, including waist belt 72, are most clearly depicted in FIG. 2, which will now be addressed.

FIG. 2 shows a front view of shoulder brace 10 in accordance with the present invention and being worn by a user. Shoulder brace 10 is put on by passing the arm 15 of the user into the sleeve portion 12 until the shoulder area 27 of the user is covered by shoulder portion 14. The front torso strap 28 extends from the shoulder area 27 where front shoulder end 32 meets shoulder member 14 and crosses over the chest area 81 of the user to the back area 82 at a point below the opposite shoulder 83 (as best shown in FIG. 3). Front side strap 52 extends downward from shoulder member 14 to back area 82 (as best shown in FIG. 4). Both front torso strap 28 and front side strap 52 are then attached to waist belt 72 (as discussed below) after waist belt 72 is put on by the user. Waist belt 72 is worn by overlapping belt end 80 onto free end 82 of waist belt 72 and applying tactile pressure to the area of overlap strip 78. This releasably fixes waist belt 72 in tension about waist region 79 of the user. The amount of tension may be adjusted based upon the placement of overlap strip 78, i.e., amount of overlap, on free end 82. By way of example but not of limitation, overlap strip 78 may be of a synthetic material that releasably adheres when free end 82 is overlapped and tactile force applied upon belt end 80 of waist belt 72.

FIG. 3 is a first side view of the preferred embodiment of shoulder brace 10 in accordance with the present invention as being worn by a user. As can be seen, front torso strap 28 passes under the shoulder area 83 that is on the opposite side of the body from shoulder 27 having shoulder brace 10. Front anchor end 34 extends down to waist belt 72 and, when shoulder brace 10 is being put on, is pulled downward and passed through a first anchor loop 77A. Front anchor end 34 is then folded back over loop 77A and pressure applied thereto so that first fastening strip 48 contacts and releasably adheres to front torso strap 28. This folding motion is shown by directional arrow 85.

Similarly, back torso strap 30 passes from where it adjoins the shoulder member 14 at shoulder area 27 down across the back 82 and to a position under the opposite shoulder 83. Back anchor end 38 extends down to waist belt 72 and is pulled downward and passed through a second anchor 77B. Back anchor end is then folded back over loop 77B and second fastening strip 50 releasably adhered thereto. It is important to note that torso straps 28 and 30 cross at a point (indicated generally at 88) below the shoulder area 83 opposite the shoulder brace 10. Thus, back anchor end 38 of torso strap 30 is passed through one of the plurality of loops 77 on waist belt 72 at a point more forward on the body than the point through which front anchor end 34 is passed. It should be understood that anchor ends 34 and 38 may be secured to waist belt 72 by any variety of means and methods; for example and without limitation, an adjustable snap or button closure system.

Turning now to address FIG. 4, FIG. 4 is a second side view of shoulder brace 10 in accordance with the present invention. FIG. 4 depicts the side of the body upon which shoulder brace 10 is being worn When shoulder brace 10 is put on front resilient side strap 52 passes under the shoulder area 27 and crosses downward the side of the body to waist belt 72. Front engagement end 58 of front resilient side strap 52 is then pulled downward and passed through a first waist loop 77C on loop surface 74 and folded back over loop 77C. (This folding motion is shown by directional arrow 87.) Pressure may in turn be applied to first coupling strip 68 on outer surface 64 of front resilient strip 52. This tactile pressure causes coupling strip 68 on outer surface 64 to releasably adhere to strap 52.

Similarly, back resilient side strap 54 passes downward from sleeve portion 12 underneath shoulder area 27 to a position on the side of the body forward of shoulder area 27. Back engagement end 62 of back resilient side strap 54 is then pulled downward and passed through second waist loop 77D on loop surface 74 of waist belt 72. Back engagement end 62 is then folded up over same second waist loop 77D and pressed to outer surface 66 of back resilient side strap 54. This tactile pressure causes coupling strip 70 (shown in shadow in FIG. 4) on outer surface 66 to releasably adhere to same outer surface 66 of back resilient side strap 54. As was seen in connection with torso straps 28 and 30, resilient side straps 52 and 54 cross over at a point below the shoulder area 27. Back engagement end 62 of back resilient side strap 54 passes through loop 77D on waist belt 72 at a point more forward on the body than the point where front engagement end 58 of front resilient side strap 52 contacts waist belt 72. From the above description it should be clear that the wearer may alter the support afforded by shoulder brace 10 by varying the tension applied to resilient torso straps 28 and 30 and resilient side straps 52 and 54. The particular rehabilitative or preventive needs of the individual should, of course, be considered when the determination as to tension and support is made.

Figure 5:
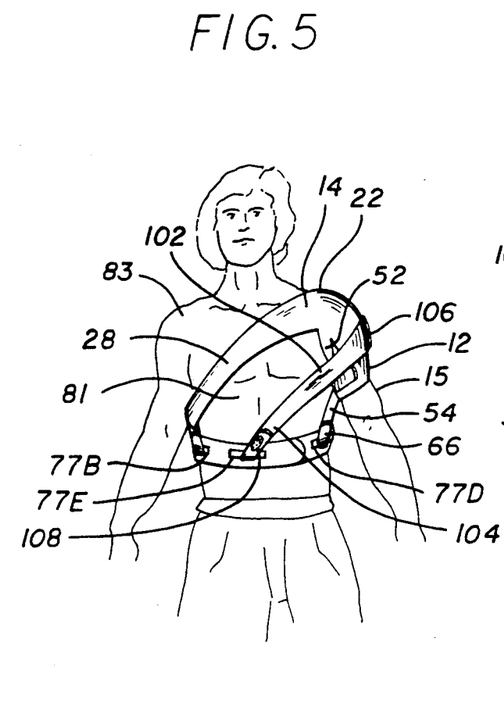
FIG. 5 is a front view of an alternative exemplary embodiment of a shoulder brace in accordance with the present invention and being worn by a user.
Figure 6:
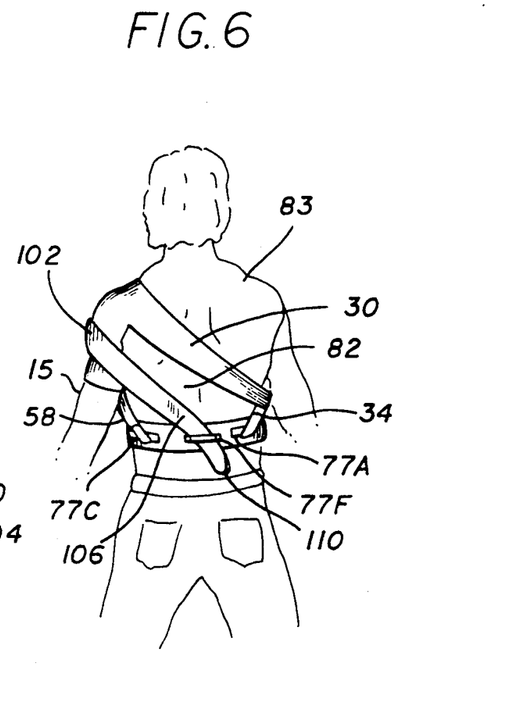
FIG. 6 is a rear view of the alternative exemplary embodiment shoulder brace as shown in FIG. 5.

Referring now to FIGS. 5 and 6, a first alternative exemplary embodiment of a shoulder brace is illustrated in association with the embodiment of FIGS. 1 through 4. The shoulder brace is generally indicated with the same parts having the same reference numerals as the shoulder brace parts heretofore described with regard to FIGS. 1 through 4. In this first alternative exemplary embodiment, shoulder harness 10 includes an abduction strap 102. Abduction strap 102 includes a front abduction end 104 and a back abduction end 106. Front and back abduction ends 104 and 106 include front abduction anchor 108 and back abduction anchor 110, respectively. As shown in FIG. 5, abduction strap 102 is attached to waist belt 72 by passing front abduction end 104 through waist loop 77E and then looping front abduction anchor 108 over loop 77E and back on to front abduction end 104. As shown in shadow in FIG. 5, front abduction strap 102 engages with front abduction end 104 by a hook-and-loop system, or other type, of fastening means. Abduction strap 102 then is pulled upward over the upper portion of arm 15 of the user, at upper sleeve area 18, and down across the back 82 of the user (as best shown in FIG. 6).

Turning to address FIG. 6, then, FIG. 6 is a rear view of the alternative exemplary embodiment shoulder brace as shown in FIG. 5. Abduction strap 102 crosses down the back 82 to waist loop 77F. The attachment method of abduction strap 102 to waist belt 72 by back abduction end 106 is similar to that discussed above with respect to FIG. 5 and front abduction end 104. Back abduction end 106, which includes a back abduction anchor 110, is pulled downward and passed through and back over loop 77F. Back abduction anchor 110 is then releasably secured to back abduction end 106. In FIG. 6, back abduction anchor 110 is shown prior to being folded over loop 77F and releasably secured to back abduction end 106. In combination with resilient torso straps 28 and 30, and resilient side straps 52 and 54, abduction strap 102 serves to limit the amount of abduction motion of the user as may be required in certain injury rehabilitative and/or preventive situations. It should be noted that abduction strap 102 also serves to additionally limit, to a degree, the amount of external rotation movement of the arm and shoulder. This external rotation movement, however, is more particularly addressed by the second alternative exemplary embodiment of the present invention, which is discussed immediately below.

Figure 7:
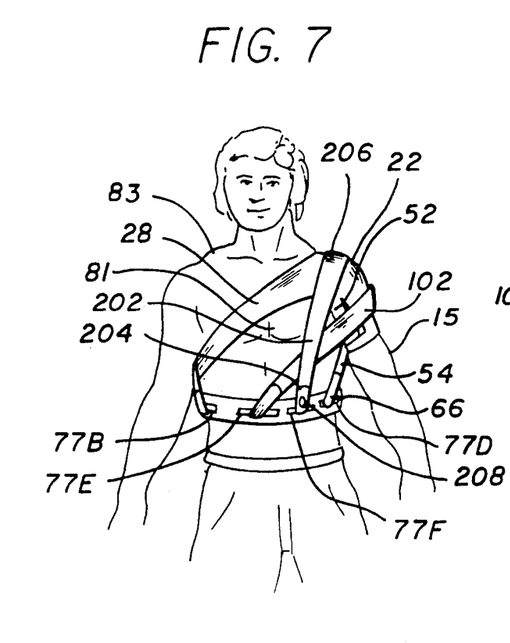
FIG. 7 is a front view of a second alternative exemplary embodiment of a shoulder brace in accordance with the present invention and being worn by a user.
Figure 8:
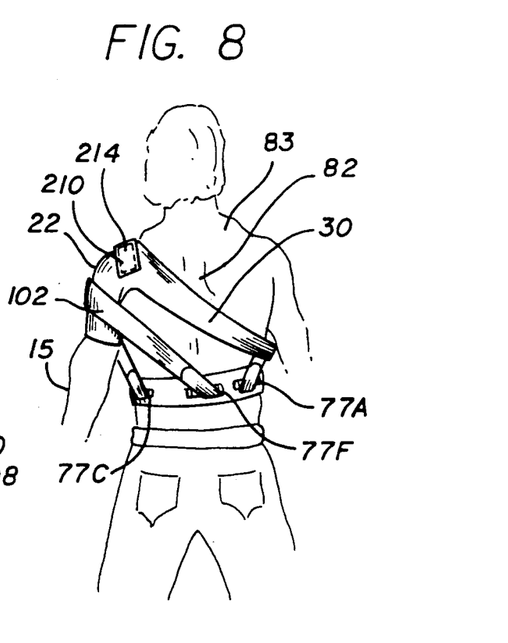
FIG. 8 is a rear view of the second alternative exemplary embodiment shoulder brace as shown in FIG. 7.

Referring now to FIGS. 7 and 8, a second alternative exemplary embodiment of a shoulder brace in accordance with the present invention will be explained. The shoulder brace parts in this instant embodiment which are the same as those previously discussed with regard to the earlier embodiments of FIGS. 1 through 6 are given the same reference numerals as before. FIG. 7 is a front view of a second alternative exemplary embodiment of a shoulder brace in accordance with the present invention and being worn by a user. Preliminarily, it is noted that this embodiment includes resilient torso straps 28 and 30, and resilient side straps 52 and 54, as well as abduction strap 102, as were previously discussed. As shown in FIG. 7, a rotation strap 202 has a rotation waist end 204 and a rotation shoulder end 206. Rotation waist end 204 and rotation shoulder end 206 include first and second rotation anchors 208 and 210, respectively. When rotation strap 202 is worn, rotation waist end 204 is passed through belt loop 77G and back over belt loop 77G so that first rotation anchor 208 may then be secured to rotation waist end 204 by utilization of a, for example, hook-and-loop type fastening means. Rotation strap 202 is pulled upward across chest 81 to the shoulder area 27 and rotation shoulder end 206 releasably secured to top portion 22 of shoulder brace 10. As shown in this embodiment, second rotation anchor 210 on rotation shoulder end 206 comprises a hook-and-loop type rotation fastening means 214 (as shown in shadow). Once affixed securely in place, rotation strap 202 limits, to a predetermined amount depending upon the tension or tightness employed in securing rotation strap 202 in place, the amount of external rotation that the arm 15 may undergo.

Figure 9:
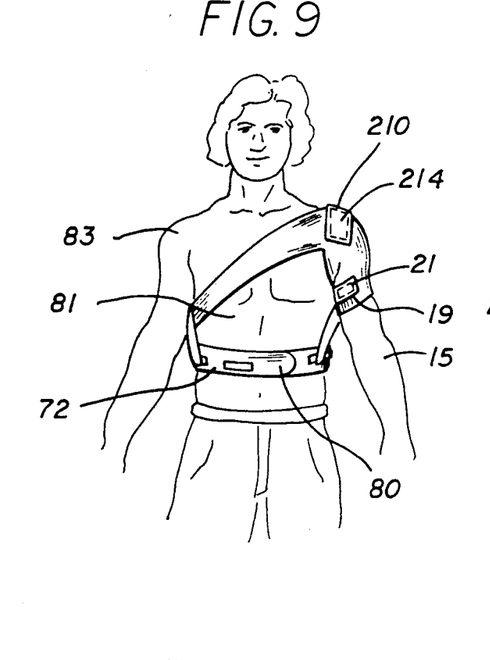
FIG. 9 is a front view of a third alternative exemplary embodiment of a shoulder brace in accordance with the present invention and being worn by a user.
Figure 10:
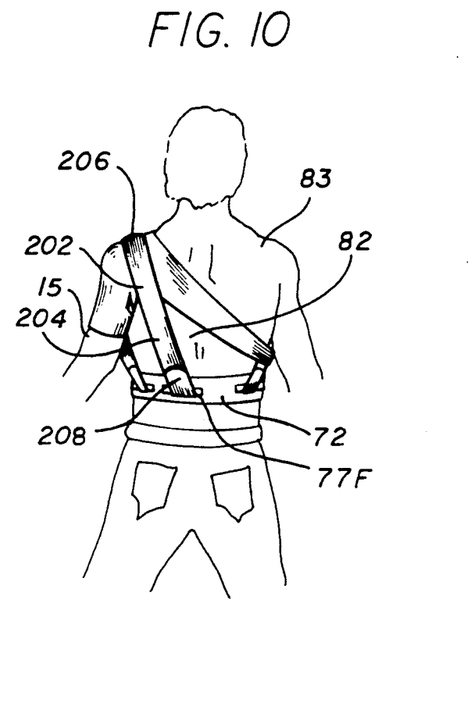
FIG. 10 is a rear view of the alternative exemplary embodiment shoulder brace as shown in FIG. 9.

It is contemplated that rotation strap 202 may be utilized without also utilizing abduction strap 102. Such an arrangement, as shown in FIGS. 9 and 10, may be desirable where, for example, an injury has been suffered to muscles or tendons that impact external rotation motion, but the muscles related to the abduction motion are entirely or substantially unaffected. Addressing FIGS. 9 and 10 with more particularity, FIG. 9 is a front view of a third alternative exemplary embodiment of a shoulder brace in accordance with the present invention and being worn by a user; and, FIG. 10 is a rear view of the third alternative exemplary embodiment shoulder brace as shown in FIG. 9. Reference numerals employed in these figures which are the same as those hereinbefore indicate the same parts here as before. As shown in FIGS. 9 and 10, rotation strap 202 includes rotation waist end 204 and rotation shoulder end 206 having first and second rotation anchors 208 and 210, respectively. In contrast to the utilization of rotation strap 202 as shown in FIGS. 7 and 8, rotation waist end 204 is shown in FIG. 9 to pass through a belt loop 77F and back over belt loop 77F so that first rotation anchor 208 may be secured on the backside of the user to rotation waist end 204 by utilization of a hook-and-loop type fastening means. Rotation strap 202 is pulled upward and passes up the back 82 of the user to the shoulder area 27 where rotation shoulder end 206 is releasably secured to top portion 22 of shoulder brace 10 (best shown in FIG. 9). As shown in this embodiment, second rotation anchor 210 on rotation shoulder end 206 comprises a hook-and-loop type rotation fastening means 214 (as shown in shadow). The decision to pass rotation strap 202 across the front of the user (as shown in FIGS. 7 and 8) or the back of the user (as shown in FIGS. 9 and 10) may be based upon comfort, the type of injury and any other of a number of medical and personal comfort concerns.

Figure 11:
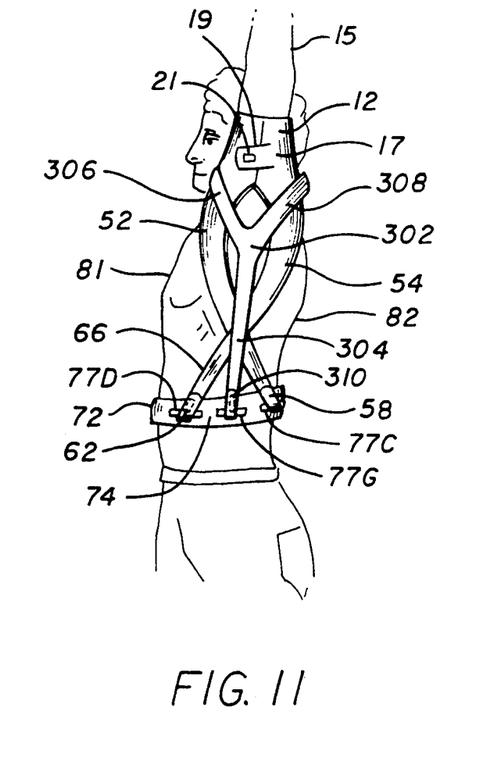
FIG. 11 is a side view of a fourth alternative exemplary embodiment of a shoulder brace in accordance with the principles of the present invention and being worn by a user.
Figure 12:
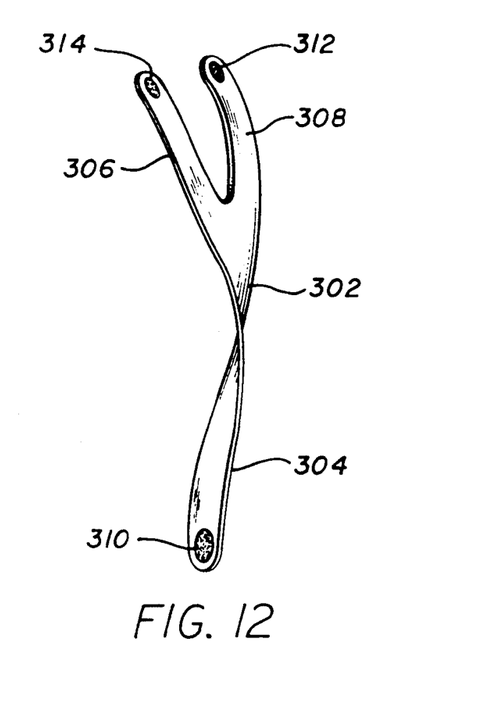
FIG. 12 is a front perspective view of an alternative exemplary embodiment of the belt portion of the shoulder brace in accordance with the principles of the present invention.

Turning now to address FIG. 11, FIG. 11 is a side view, similar to that view of FIG. 3, of a fourth alternative exemplary embodiment of a shoulder brace in accordance with the principles of the present invention and being worn by a user. In this embodiment, shoulder brace parts that are the same as those heretofore discussed in connection with the preferred and first through third alternative exemplary embodiments of FIGS. 1 through 10 are given the same reference numerals as before. Front and back resilient side straps 52 and 54, respectively, cross down the side of the user from the shoulder area 72 and attach, as previously discussed in detail in connection with FIG. 3, to waist belt 72. Also shown in FIG. 11 is Y-strap 302. Y-strap 302 includes Y-anchor end 304 and first and second Y-shoulder ends 306 and 308, respectively. The method of affixing Y-anchor end 304 of Y-strap 302 to waist belt 72 is similar to the earlier discussed methods of, for example, rotation strap 202 and abduction strap 102. Specifically, Y-anchor end 304 is passed through and back over a belt loop 77G so that a Y-anchor tab 310 releasably secures to Y-anchor end 304. Y-strap 302 is then pulled upward so that first and second Y-shoulder ends 306 and 308 travel up the side torso of the user and releasably secure to top portion 22 of shoulder brace 10. While the attachment area is not shown in FIG. 11, it should be understood that each of first and second Y-shoulder ends 306 and 308 include first and second Y-affixing tabs 312 and 314 (best shown in FIG. 12) for releasably securing Y-strap 302 to top position 22. Y-affixing tabs 312 and 314 are shown in FIG. 12 to include a hook-and-loop type fastening means (similar to those previously described herein). When worn, Y-strap 302 provides both abductive and external rotation support for the user.

As clearly depicted in FIG. 12, Y-strap 302 is preferably made of a flexible material so that it may bend to conform with the torso of the individual user. A "custom" fit that maximizes the rehabilitative, as well as preventive, functions of the invention may thus be obtained. The material comprising shoulder brace 10 of the present invention should similarly exhibit the requisite resiliency to meet the above-described functions. By way of example, the shoulder brace 10 may be formed of a neoprene rubber. Neoprene rubber has been found to be the preferable material because of its water resistant characteristic and light weight. Additionally, other rubbers or various engineering plastics or materials having the requisite characteristics of conformability and/or resiliency may be used. By way of example but not of limitation, nylon is a suitable material that may also be provided appropriate fastening means enabling shoulder brace 10 to be readily adjusted to the size of the user.

Figure 13:
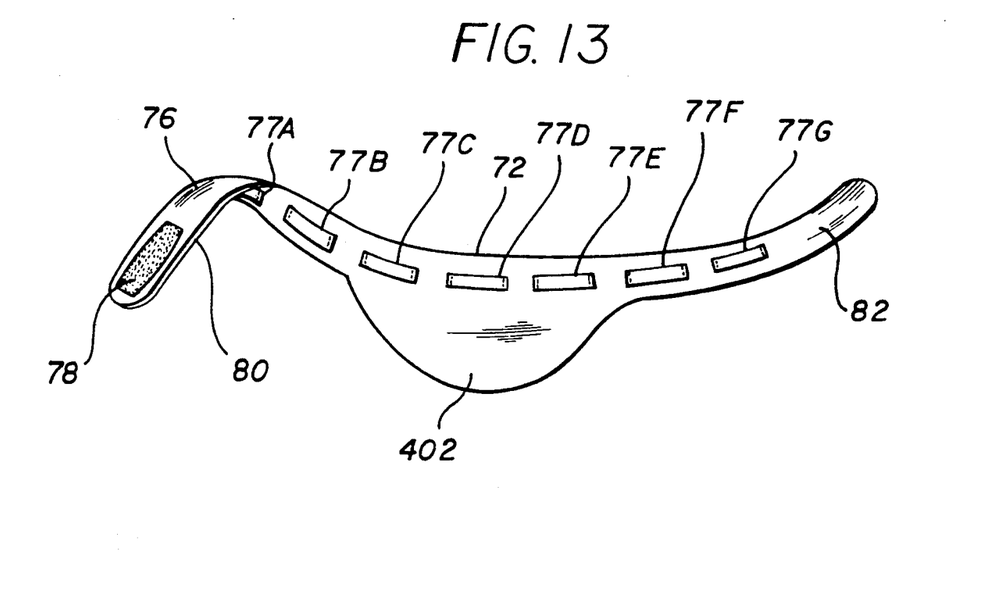
FIG. 13 is a front perspective view of a second alternative exemplary embodiment of the belt portion of the shoulder brace in accordance with the principles of the present invention.
Figure 14:
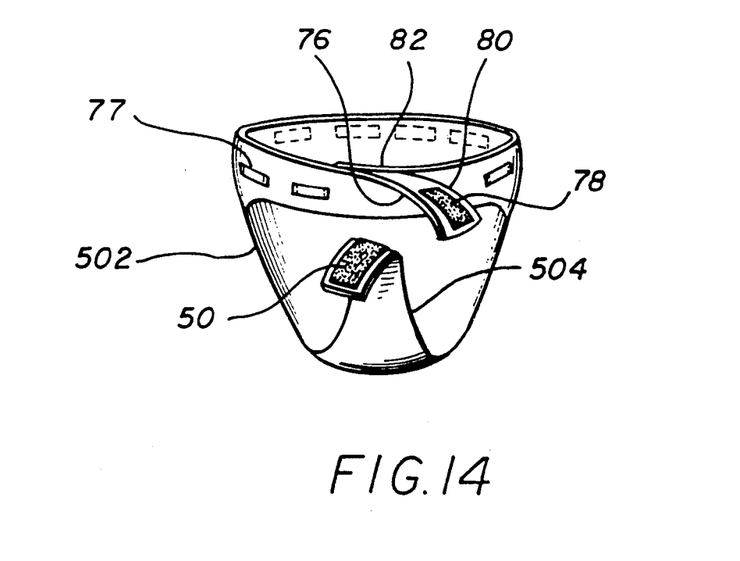

Further with respect to waist belt 72, it should be understood that waist belt 72 may take on a variety of configurations. Referring now to FIGS. 13 and 14, first and second alternative exemplary embodiments of the waist belt of the present invention are shown. Turning first to FIG. 13, FIG. 13 is a front perspective view of an alternative exemplary embodiment of the belt portion of the shoulder brace in accordance with the principles of the present invention. It should be understood that the attachment methods of waist belt 72 about the waist of the user and to the shoulder brace 10 are the same as was discussed in connection with the preferred embodiment of waist belt 72 with respect to FIGS. 1 through 11. The alternative embodiment of the waist belt being generally indicated with the same parts having the same reference numerals as the waist belt 72 parts heretofore described with regards to FIGS. 1 through 3. As shown in FIG. 13, waist belt 72 includes a posterior piece 402 which may be tucked into the pants, sweatsuit, or other clothing item (not shown) of the user. While waist belt 72 utilizes belt overlap strap 78 on belt end 80 in order to easily and securely adjust to fit the waist size of most individuals, posterior piece 402 also assists in securing waist belt 72 to the proper position on the body of the user and further decreases the possibility that waist belt 72 will be pulled up and out of position on the user. This anchoring attribute helps ensure that shoulder brace 10 is held securely about the user and the proper and desired tension maintained.

Turning now to FIG. 14, FIG. 14 is a front perspective view of a second alternative exemplary embodiment of the belt portion of the shoulder brace in accordance with the principles of the present invention. This second alternative exemplary embodiment of waist belt 72 includes a posterior member 502. Posterior member 502 is shown to be a "beaver tail" type design wherein the tail end 504 of posterior member 502 wraps around the crotch area of the user and fastens to waist belt 72 near belt end 80. As shown in this second alternative exemplary embodiment, tail end 504 includes a tail fastening means 506 which is shown to be a releasable hook-and-loop type fastening means. As was discussed with respect to the first alternative exemplary embodiment of FIG. 13, posterior member 502 helps secure waist belt 72 about the user, thereby assuring the proper fit, and maximum rehabilitative and preventive function of shoulder brace 10.

Having thus described a preferred exemplary embodiment of the shoulder brace in accordance with the present invention as well as first through fourth alternative exemplary embodiments, it should be apparent to those skilled in the art that various additional objects and advantages have been attained by the within invention and that a variety of modifications, adaptions and equivalent constructions can be made within the scope and spirit of the present invention and all such changes, modifications, adaptions and equivalent constructions coming within the scope of the appended claims are embraced thereby, being limited only by the appended claims.

I claim:

1. A shoulder brace comprising:
    a resilient shoulder means conformable to the shoulder and upper arm of a wearer, said shoulder means including an adjustable sleeve portion having a means for adjustably attaching said sleeve portion to the upper arm and a shoulder member attached to said sleeve portion and covering the shoulder and extending downward therefrom;
    a plurality of resilient torso straps each having a shoulder end fixedly attached to said shoulder means and an anchor end;
    a plurality of resilient side straps each having a sleeve end fixedly attached to said shoulder means and a waist end; and
    a belt means for engaging each of said anchor ends and said waist ends.

2. The shoulder brace as defined in claim 1, wherein said belt means further comprises:
    a waist belt;
    an overlap means affixed to said waist belt for releasably affixing said waist belt about the waist;
    a plurality of loop means in spatial relationship about said waist belt, said plurality of loop means for removably securing each of said anchor ends and said waist ends to said waist belt.

3. The shoulder brace as defined in claim 2, wherein said belt means further comprises a means for securing said shoulder brace to the wearer.

4. The shoulder brace as defined in claim 1, wherein each of said plurality of resilient torso straps includes an anchoring means affixed on said anchor end.

5. The shoulder brace as defined in claim 1, wherein each of said plurality of resilient side straps includes a coupling means affixed on said waist end.

6. The shoulder brace as defined in claim 2, wherein said overlap means is a hook-and-loop type of fastening means.

7. The shoulder brace as defined in claim 3, wherein said anchor means is a hook-and-loop type fastening means.

8. The shoulder brace as defined in claim 4, wherein said coupling means is a hook-and-loop type fastening means.

9. The shoulder brace as defined in claim 2, wherein said plurality of loop means includes:
    first and second anchor loops spatially positioned on said waist belt; and
    first and second waist loops spatially positioned on said waist belt.

10. The shoulder brace as defined in claim 1, wherein said shoulder brace consists of neoprene rubber.

11. In a shoulder brace for restricting movement of the ball of the upper arm out of the socket of the shoulder and permitting free movement of the arm, the combination of:
  (a) a resilient shoulder means for enveloping the shoulder and the upper arm, said shoulder means comprising:
    i) an adjustable sleeve portion encasing the upper arm,
    ii) a C-shaped shoulder member covering the shoulder and integral with said sleeve portion;
  (b) a plurality of resilient torso straps, each of said torso straps comprising:
    i) a shoulder end attached to said shoulder means and an anchor end;
    ii) an anchoring means affixed to said anchor end;
  (c) a plurality of resilient side straps, each of said side straps comprising:
    i) a sleeve end, attached to said shoulder means, and a waist end,
    ii) a coupling means affixed to said waist end;
  (d) a belt means, said belt means comprising:
    i) a waist belt,
    ii) an overlap means affixed to said waist belt for releasably affixing said waist belt about the waist,
    iii) a plurality of fastening means in spatial relationship about said waist belt, said plurality of fastenings means for removably securing each of said anchor ends and said waist ends to said waist belt.

12. The shoulder brace as defined in claim 11, wherein said anchoring means and said coupling means are a hook-and-loop type fastening means.

13. The shoulder brace as defined in claim 11, wherein said shoulder brace further comprises a resilient abduction means for limiting the amount of abductive movement of the arm.

14. The shoulder brace as defined in claim 13, wherein said abduction means comprises an abduction strap having front and back abduction ends, each of said abduction ends including abduction anchor ends removably attachable to said belt means.

15. The shoulder brace as defined in claim 11, wherein said shoulder brace further comprises a rotation means for limiting the amount of external rotation movement of the arm.

16. The shoulder brace as defined in claim 15; wherein said rotation means comprises a rotation strap having a rotation shoulder end and a rotation waist end; said rotation shoulder end removably attachable to said shoulder means and said rotation waist end removably attachable to said belt means.

17. A neoprene rubber shoulder brace for restricting movement of the ball of the upper arm out of the socket of the shoulder and providing support to the muscles, tendons and ligaments in the shoulder area and permitting free movement of the arm, said shoulder brace comprising:
  a resilient shoulder means conformable to the shoulder and upper arm of a wearer, said shoulder means including sleeve portion and a C-shaped shoulder member attached to said sleeve portion;
  a plurality of resilient torso straps, each of said torso straps having a shoulder end attached to said shoulder means and an anchor end, said anchor end including an anchoring means;
  a plurality of resilient side straps, each of said side straps having a sleeve end attached to said shoulder means and a waist end, said waist end including a coupling means;
  a resilient abduction strap for limiting the amount of abductive movement of the arm, said abduction strap having front and back abduction ends, each of said abduction ends including abduction anchor means;
  a resilient rotation strap for limiting the amount of external rotation movement of the arm, said rotation strap having a rotation shoulder end attachable to said shoulder means and a rotation waist end including a rotation anchor means;
  a resilient belt means for securing said shoulder brace about the waist, said belt means including a waist belt, an overlap means affixed to said waist belt for releasably securing said waist belt in tension about the waist and a plurality of loop means in spatial relationship about said waist belt, said plurality of loop means including first and second anchor loops for spatially positioning each of said anchor ends on said waist belt, first and second waist loops for spatially positioning each of said waist ends on said waist belt, first and second abduction loops for spatially positioning each of said abduction ends on said waist belt, and a rotation loop for spatially positioning said rotation waist end on said waist belt, and said anchoring means for releasably securing said anchor ends on said waist belt, said coupling means for releasably securing said waist ends to said waist belt, said abduction anchor means for releasably securing said abduction straps to said waist belt and said rotation anchor means for releasably securing said rotation straps to said waist belt.

* * * * *